United States Patent
Lugar, III et al.

(10) Patent No.: US 10,603,320 B2
(45) Date of Patent: Mar. 31, 2020

(54) COMPOUNDS USEFUL FOR INHIBITING ROR-GAMMA-T

(71) Applicant: Eli Lilly and Company, Indianapolis, IN (US)

(72) Inventors: Charles Willis Lugar, III, McCordsville, IN (US); John Richard Morphy, Surrey (GB); Timothy Ivo Richardson, Zionsville, IN (US); Helene Catherine Eugenie Rudyk, Surrey (GB); Selma Sapmaz, Basingstoke (GB); Ryan Edward Stites, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/482,602

(22) PCT Filed: Feb. 27, 2018

(86) PCT No.: PCT/US2018/019907
§ 371 (c)(1),
(2) Date: Jul. 31, 2019

(87) PCT Pub. No.: WO2018/160547
PCT Pub. Date: Sep. 7, 2018

(65) Prior Publication Data
US 2020/0009139 A1 Jan. 9, 2020

Related U.S. Application Data

(60) Provisional application No. 62/466,110, filed on Mar. 2, 2017.

(51) Int. Cl.
C07D 495/20 (2006.01)
A61K 31/506 (2006.01)
C07D 495/14 (2006.01)

(52) U.S. Cl.
CPC .......... *A61K 31/506* (2013.01); *C07D 495/14* (2013.01); *C07D 495/20* (2013.01)

(58) Field of Classification Search
CPC ........................... C07D 495/14; C07D 495/20
See application file for complete search history.

(56) References Cited

U.S. PATENT DOCUMENTS

| 9,598,431 B1* | 3/2017 | Morphy | C07D 495/20 |
| 9,868,748 B2 | 1/2018 | Claremon et al. | |
| 2011/0118251 A1* | 5/2011 | Benito Collado ... | C07D 495/20 514/230.8 |
| 2012/0214784 A1* | 8/2012 | Benito Collado ... | C07D 495/20 514/210.2 |
| 2014/0309251 A1* | 10/2014 | Kehn | A61K 31/435 514/278 |
| 2017/0066781 A1* | 3/2017 | Morphy | A61K 31/506 |

FOREIGN PATENT DOCUMENTS

| WO | 2015/101928 A1 | 7/2015 |
| WO | 2017/044410 A1 | 3/2017 |

OTHER PUBLICATIONS

J. P. Sherlock et al., 18 Nature Medicine, 1069-1077 (2012) (Year: 2012).*
S. P. Raychaudhuri et al., 35 Clinical Rheumatol, 1437-1441 (2016) (Year: 2016).*
K. Venken et al., 17 Curr Rheumatol Rep (2015) (Year: 2015).*

* cited by examiner

*Primary Examiner* — Alexander R Pagano
(74) *Attorney, Agent, or Firm* — Nelsen L Lentz

(57) ABSTRACT

The present invention provides novel ROR gamma-t inhibitors and pharmaceutical compositions thereof. Formula (I).

15 Claims, No Drawings

COMPOUNDS USEFUL FOR INHIBITING ROR-GAMMA-T

The present invention relates to compounds useful for inhibiting retinoic acid receptor-related orphan receptor gamma-t (RORγt), pharmaceutical compositions, and methods for treating diseases related to RORγ activity.

The retinoic acid receptor-related orphan receptors (RORs) are members of the nuclear receptor (NR) superfamily identified as important pathological regulators in many diseases. The ROR subfamily consists of RORα, RORβ, and RORγ. The mouse and human RORγ gene generates two isoforms, γ1 and γ2, the latter most commonly referred to as γt. RORγt signaling, often in response to IL-23/IL-23 receptor signaling, is required for the differentiation of naive CD4+ T-cells into a subset of T-cells designated Th17, which are distinct from the classical Th1 and Th2 cells, and supports their maintenance. Th17 cells produce interleukin-17A (IL-17) and IL-17F. In addition, Th17 cells produce a range of other factors known to drive inflammatory responses, including tumor necrosis factor-alpha (TNF-α), interleukin-6 (IL-6), GM-CSF, CXCL1 and CCL20. NK cells and innate lymphoid cells such as lymphoid tissue inducer (LTi)-like cells express IL-23 receptor and RORγt and produce IL-17 in response to stimulation and IL-23. There is substantial evidence that IL-23-responsive, RORγt, and IL-17-expressing cells are associated with autoimmune diseases (AI), inflammatory diseases, and cancer. Thus, targeted inhibition of RORγt may be important to reducing the pathogenesis of those diseases.

AI diseases are chronic conditions for which no cure currently exists. Treatment of AI diseases typically involves an attempt to control the process of the disease and decrease the symptoms by administering anti-inflammatory, anti-pain, or immunosuppressant medications. Unfortunately, the use of anti-inflammatory and anti-pain medications is sometimes ineffective and the use of immunosuppressants often leads to devastating long-term side effects. The most significant side effects of immunosuppressant drugs are an increased risk of infection and a higher risk of cancer.

Natural and synthetic ligands to RORγt have been identified. Small molecule inhibitors against RORγt have been reported in the literature for AI. See WO 2015/017335 and WO 2014/179564. However, the prevalence of AI diseases coupled with the ineffectiveness or devastating side effects of current treatments necessitate that more treatment choices be available to patients. Targeting RORγt may present an advantage over current AI therapies by maximizing the therapeutic benefit by targeting pathogenic immune cells while minimizing the risk of suppression of host defenses.

The present invention provides novel compounds that are RORγt inhibitors. Such new compounds could address the need for potent, effective treatment of uveitis, multiple sclerosis, rheumatoid arthritis, graft versus host disease, Crohn's disease, other inflammatory bowel diseases, cancer, psoriasis, and seronegative spondylarthropathies, such as axial spondyloarthritis, ankylosing spondylitis, and psoriatic arthritis.

The present invention provides compounds of the Formula:

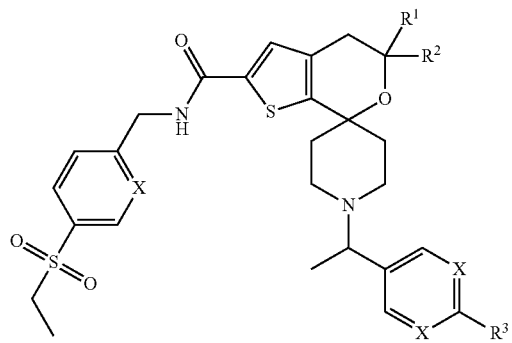

wherein
X is independently —N— or —CH—;
$R^1$ and $R^2$ are both $CH_3$;
or $R^1$ and $R^2$ can be joined together to form a three-membered carbocyclic ring;
$R^3$ is —CN or —$CF_3$;
or a pharmaceutically acceptable salt thereof.

The present invention also provides a method for the treatment of psoriasis in a patient comprising administering to a patient in need thereof a compound of the present invention, or a pharmaceutically acceptable salt thereof. Further, the present invention provides a method for the treatment of seronegative spondylarthropathies in a patient comprising administering to a patient in need thereof a compound of the present invention, or a pharmaceutically acceptable salt thereof. In said embodiment, seronegative spondylarthropathies are axial spondyloarthritis, ankylosing spondylitis, or psoriatic arthritis.

The present invention provides a pharmaceutical composition comprising a compound of the invention, or a pharmaceutically acceptable salt thereof, in combination with one or more pharmaceutically acceptable carriers, diluents, or excipients. In a further embodiment, the composition further comprises one or more other therapeutic agents. In a further embodiment, the present invention provides a pharmaceutical composition for the treatment of psoriasis comprising a compound of the invention, or a pharmaceutically acceptable salt thereof, in combination with one or more pharmaceutically acceptable carriers, diluents, or excipients. In yet a further embodiment, the present invention provides a pharmaceutical composition for the treatment of seronegative spondylarthropathies comprising a compound of the invention, or a pharmaceutically acceptable salt thereof, in combination with one or more pharmaceutically acceptable carriers, diluents, or excipients. In said embodiment, seronegative spondylarthropathies are axial spondyloarthritis, ankylosing spondylitis, or psoriatic arthritis.

Further, the present invention provides a compound of the invention, or a pharmaceutically acceptable salt thereof, for use in therapy, in particular for the treatment of psoriasis. Even further, the present invention provides a compound of the invention, or a pharmaceutically acceptable salt thereof, for use in the treatment of psoriasis. In a further embodiment, the present invention provides the use of a compound of the invention, or a pharmaceutically acceptable salt thereof, for the manufacture of a medicament for the treatment of psoriasis.

Further, the present invention provides a compound of the invention, or a pharmaceutically acceptable salt thereof, for use in therapy, in particular for the treatment of seronegative spondylarthropathies. Even further, the present invention provides a compound of the invention, or a pharmaceutically acceptable salt thereof, for use in the treatment of seronegative spondylarthropathies. In a further embodiment, the present invention provides the use of a compound of the invention, or a pharmaceutically acceptable salt thereof, for the manufacture of a medicament for the treatment of seronegative spondylarthropathies. In said embodiments, seronegative spondylarthropathies are of axial spondyloarthritis, ankylosing spondylitis, or psoriatic arthritis.

The present invention also encompasses intermediates and processes useful for the synthesis of a compound of the present invention.

The term "treating" (or "treat" or "treatment") as used herein refers to restraining, slowing, stopping, or reversing the progression or severity of an existing symptom, condition or disorder.

The term "spondylarthropathies" refers to a number of chronic joint diseases that generally involve the vertebral column and the areas where ligaments and tendons attach to bone. Spondylarthropathies are sometimes also called spondyloarthropathies or spondyloarthritis.

The term "seronegative" refers to a disease which is negative for rheumatoid factor.

A compound of the present invention may react to form pharmaceutically acceptable salts. Pharmaceutically acceptable salts and common methodology for preparing them are well known in the art. See, e.g., P. Stahl, et al. *Handbook of Pharmaceutical Salts: Properties, Selection and Use*, $2^{nd}$ Revised Edition (Wiley-VCH, 2011); S. M. Berge, et al., "Pharmaceutical Salts," *Journal of Pharmaceutical Sciences*, Vol. 66, No. 1, January 1977.

The skilled artisan will appreciate that a compound of the invention, as shown in (I), or pharmaceutically acceptable salt thereof, is comprised of a core that contains at least one chiral center, as represented by * below:

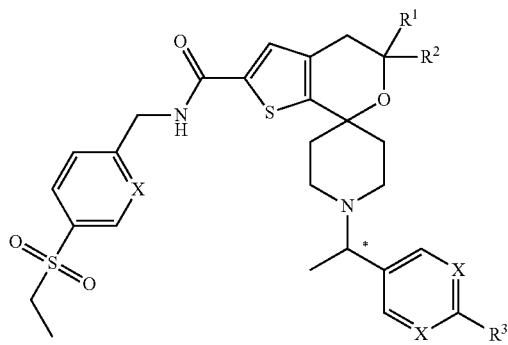

(I)

Although the present invention contemplates all individual enantiomers, as well as mixtures of the enantiomers of said compounds including racemates, the preferred compounds of the invention are represented by (II) below:

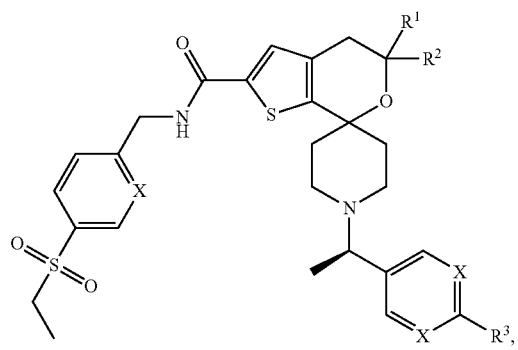

(II)

or pharmaceutically acceptable salts thereof.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers of compounds of the invention are a preferred embodiment of the invention.

A compound of the present invention is preferably formulated as pharmaceutical compositions administered by a variety of routes. Such pharmaceutical compositions and processes for preparing the same are well known in the art. See, e.g., *Remington: The Science and Practice of Pharmacy* (A. Gennaro, et al., eds., $22^{nd}$ ed., Pharmaceutical Press, 2012). More particularly preferred, is a pharmaceutical composition comprising a compounds of the formula,

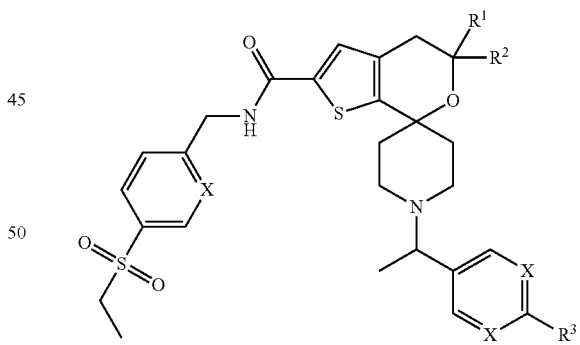

wherein

X is independently —N— or —CH—;

$R^1$ and $R^2$ are both $CH_3$;

or $R^1$ and $R^2$ can be joined together to form a three-membered carbocyclic ring;

$R^3$ is —CN or —$CF_3$; or a pharmaceutically acceptable salt thereof and one or more pharmaceutically acceptable carriers or diluents.

A preferred embodiment of the compounds of the present invention relates to compounds of the following formula,

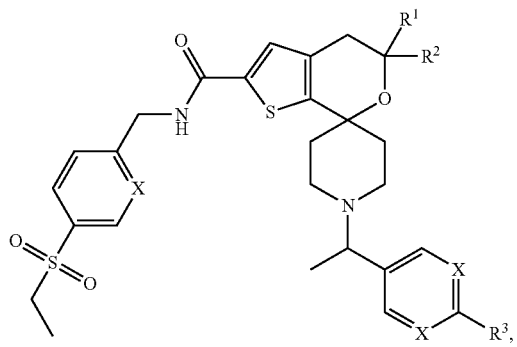

X is independently —N— or —CH—;
R¹ and R² are both CH₃;
or R¹ and R² can be joined together to form a three-membered carbocyclic ring;
R³ is —CN or —CF₃; or a pharmaceutically acceptable salt thereof.

Another preferred embodiment of the compounds of the present invention relates to compounds of the following formula,

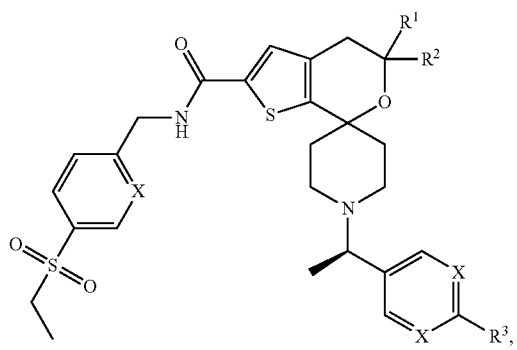

X is independently —N— or —CH—;
R¹ and R² are both CH₃;
or R¹ and R² can be joined together to form a three-membered carbocyclic ring;
R³ is —CN or —CF₃; or a pharmaceutically acceptable salt thereof.

A preferred embodiment of the compounds of the present invention relates to compounds of the following formula,

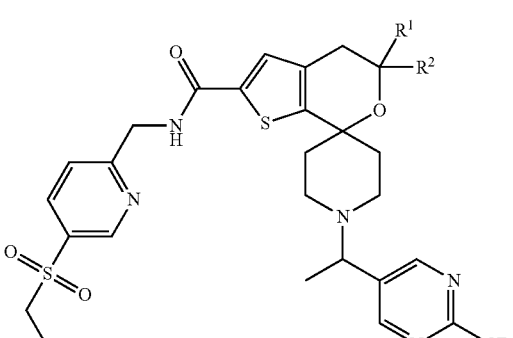

R¹ and R² are both CH₃;
or R¹ and R² can be joined together to form a three-membered carbocyclic ring; or a pharmaceutically acceptable salt thereof.

Another preferred embodiment of the compounds of the present invention relates to compounds of the following formula,

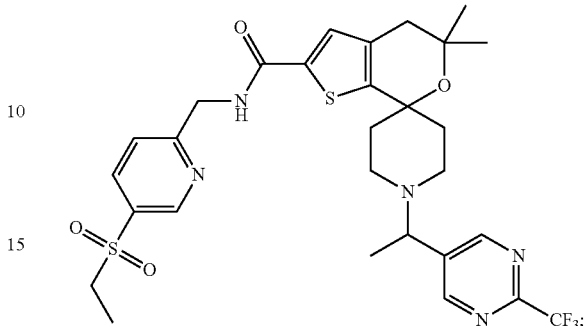

or a pharmaceutically acceptable salt thereof.

Another preferred embodiment of the compounds of the present invention relates to compounds of the following formula,

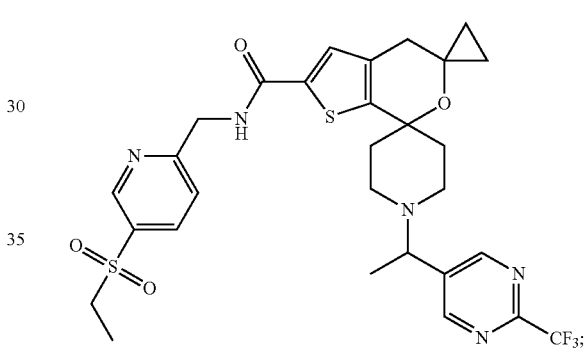

or a pharmaceutically acceptable salt thereof.

Another preferred embodiment of the compounds of the present invention relates to compounds of the following formula,

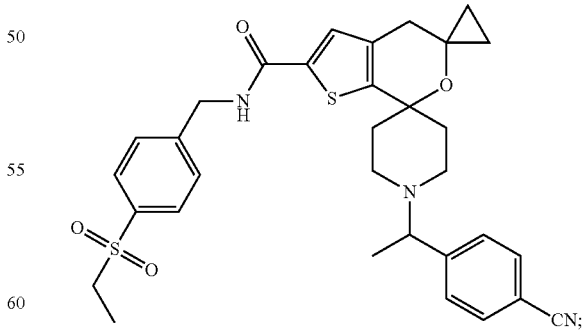

or a pharmaceutically acceptable salt thereof.

An especially preferred embodiment of the present invention relates to the compound, N-{[5-(Ethylsulfonyl)pyridin-2-yl]methyl}-5',5'-dimethyl-1-{(1R)-1-[2-(trifluoromethyl)

pyrimidin-5-yl]ethyl}-4',5'-dihydrospiro[piperidine-4,7'-thieno[2,3-c]pyran]-2'-carboxamide

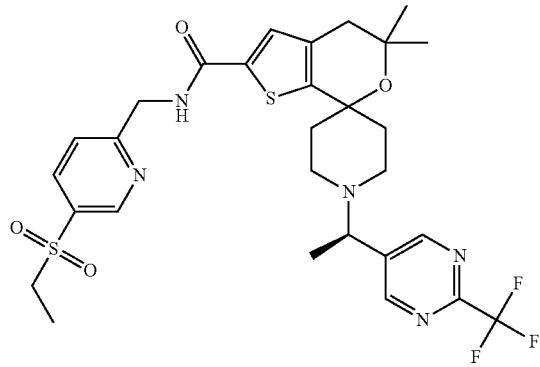 [SMILES: CCS(=O)(=O)c1ccc(CNC(=O)c2cc3c(s2)C2(CCN([C@H](C)c4cnc(C(F)(F)F)nc4)CC2)OC(C)(C)C3)nc1]

or a pharmaceutically acceptable salt thereof.

Another especially preferred embodiment of the present invention relates to the compound, N-{[5-(Ethylsulfonyl)pyridin-2-yl]methyl}-1''-{(1R)-1-[2-(trifluoromethyl)pyrimidin-5-yl]ethyl}-4'H-dispiro[cyclopropane-1,5'-thieno[2,3-c]pyran-7',4''-piperidine]-2'-carboxamide

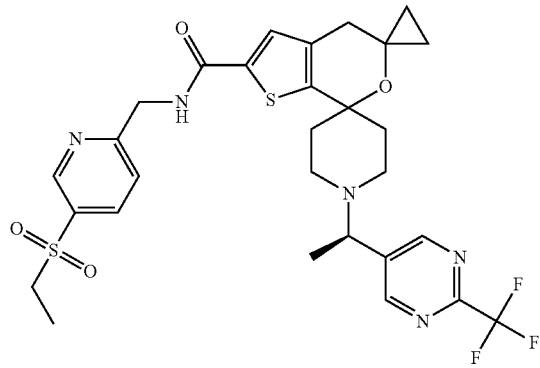 [SMILES: CCS(=O)(=O)c1ccc(CNC(=O)c2cc3c(s2)C2(CCN([C@H](C)c4cnc(C(F)(F)F)nc4)CC2)OC2(CC2)C3)nc1]

or a pharmaceutically acceptable salt thereof.

The compounds of the present invention are generally effective over a wide dosage range. For example, dosages per day fall within the range of about 1 mg to 1 g. In some instances, dosage levels below the lower limit of the aforesaid range may be more than adequate, while in other cases still larger doses may be employed while maintaining a favorable benefit/risk profile, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds or salts of the present invention. The products of each step in the Schemes below can be recovered by conventional methods well known in the art, including extraction, evaporation, precipitation, chromatography, filtration, trituration, and crystallization. In the Schemes below, all substituents unless otherwise indicated, are as previously defined. The reagents and starting materials are readily available to one of ordinary skill in the art.

Additionally, certain intermediates described in the following schemes may contain one or more nitrogen or oxygen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain stereochemical centers have been left unspecified and certain substituents have been eliminated in the following schemes for the sake of clarity and are not intended to limit the teaching of the schemes in any way. Single enantiomers or diastereomers may be prepared beginning with chiral reagents or by stereoselective or stereospecific synthetic techniques. Alternatively, the single enantiomers or racemates may be isolated from mixtures by standard chiral chromatographic or crystallization techniques at any convenient point in the synthesis of compounds of the invention by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994).

Some intermediates or compounds of the present invention may have one or more chiral centers. The present invention contemplates all individual enantiomers or diastereomers, as well as mixtures of the enantiomers and diastereomers of said compounds including racemates. It is preferred that compounds of the present invention containing at least one chiral center exist as a single enantiomer or diastereomer. The single enantiomer or diastereomer may be prepared beginning with chiral reagents or by stereoselective or stereospecific synthetic techniques. Alternatively, the single enantiomer or diastereomer may be isolated from mixtures by standard chiral chromatographic or crystallization techniques. The skilled artisan will appreciate that in some circumstances the elution order of enantiomers or diastereomers may be different due to different chromatographic columns and mobile phases. The designations "isomer 1" and "isomer 2" refer to the compounds that elute from chiral chromatography first and second, respectively, and if chiral chromatography is initiated early in the synthesis, the same designation is applied to subsequent intermediates and examples.

Certain abbreviations are defined as follows: "ACN" refers to acetonitrile; "AUC" refers to area under the curve; "BPR" refers to back pressure regulator; "BSA" refers to Bovine Serum Albumin; "DBA" refers to dilute brown non-Agouti; "DCC" refers to 1,3-dicyclohexylcarbodiimide; "DCM" refers to dichloromethane; "de" refers to diasteriometric excess; "DFT" refers to density functional theory; "DIC" refers to diisopropylcarbodiimide; "DIPEA" refers to diisopropylethylamine, N-ethyl-N-isopropyl-propan-2-amine, or N,N-diisopropylethylamine; "DMAP" refers to 4-dimethylaminopyridine; "DMEM" refers to Dulbecco's Modified Eagle's Medium; "DMF" refers to dimethylformamide; "DMSO" refers to dimethylsulfoxide; "DNA"

refers to deoxyribonucleic acid; "DPBS" refers to Dulbecco's phosphate buffered saline; "EDCI" refers to 1-(3-dimethylaminopropyl)-3-ethylcarbodiimide hydrochloride; "$EC_{50}$" refers to effective concentration at half the maximal response; "ee" refers to enantiomeric excess; "ELISA" refers to enzyme-linked immuno assay; "EtOAc" refers to ethyl acetate; "EtOH" refers to ethanol or ethyl alcohol; "$Et_2O$" refers to ethyl ether; "Ex" refers to example; "FBS" refers to Fetal Bovine Serum; "G" refers to gravitational force; "GAL" refers to beta-galactosidase DNA binding domain; "GPI" refers to glucose-6-phosphate isomerase; "HBTU" refers to (2-(1H-benzotriazol-1-yl)-1,3,3-tetramethyluronium hexafluorophosphate); "HEC" refers to hydroxy ethyl cellulose; "HEK" refers to human embryonic kidney; "HEPES" refers to 4-(2-hydroxyethyl)-1-piperazineethanesulfonic acid; "HOAt" refers to 1-hydroxy-7-azobenzotriazole; "HOBt" refers to 1-hydroxylbenzotriazole hydrate; "$IC_{50}$" refers to the concentration of an agent that produces 50% of the maximal inhibitory response possible for that agent; "IL" refers to interleukin; "ion exchange chromatography" refers to purification using ISO-LUTE® Flash SCX-2 ion exchange chromatography eluting with 2 M $NH_3$ in MeOH; "IPA" refers to isopropyl alcohol or isopropanol; "IPAm" refers to isopropylamine; "Kd" refers to constant of dissociation; "Ki" refers to inhibition constant; "min" refers to minute or minutes; "MEM" refers to Minimum Essential Medium; "MeOH" refers to methanol or methyl alcohol; "MS" refers to Mass Spectrometry; "MTBE" refers to methyl t-butyl ether; "NBS" refers to N-bromosuccinimide; "PBMC" refers to peripheral blood mononuclear cell; "PBS" refers to phosphate buffered saline, "PEM" refers to photo-elastic modulator; "Prep" refers to preparation; "RAR refers to retinoic acid receptor; "RPMI" refers to Roswell Park Memorial Institute; "RT" refers to room temperature; "$R_t$" refers to retention time; "SCX" refers to strong cation exchange; "SFC" refers to supercritical fluid chromatography; "T3P®" refers to 1-propanephosphonic anhydride solution, 2,4,6-tripropyl-1,3,5,2,4,6-trioxatriphosphorinane-2,4,6-trioxide solution or PPACA; "TEA" refers to triethylamine; "THF" refers to tetrahydrofuran; "VCD" refers to vibrational circular dichroism and "XRD": refers to X-ray powder diffraction.

In the Schemes below, all substituents unless otherwise indicated, are as previously defined. The reagents and starting materials are readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

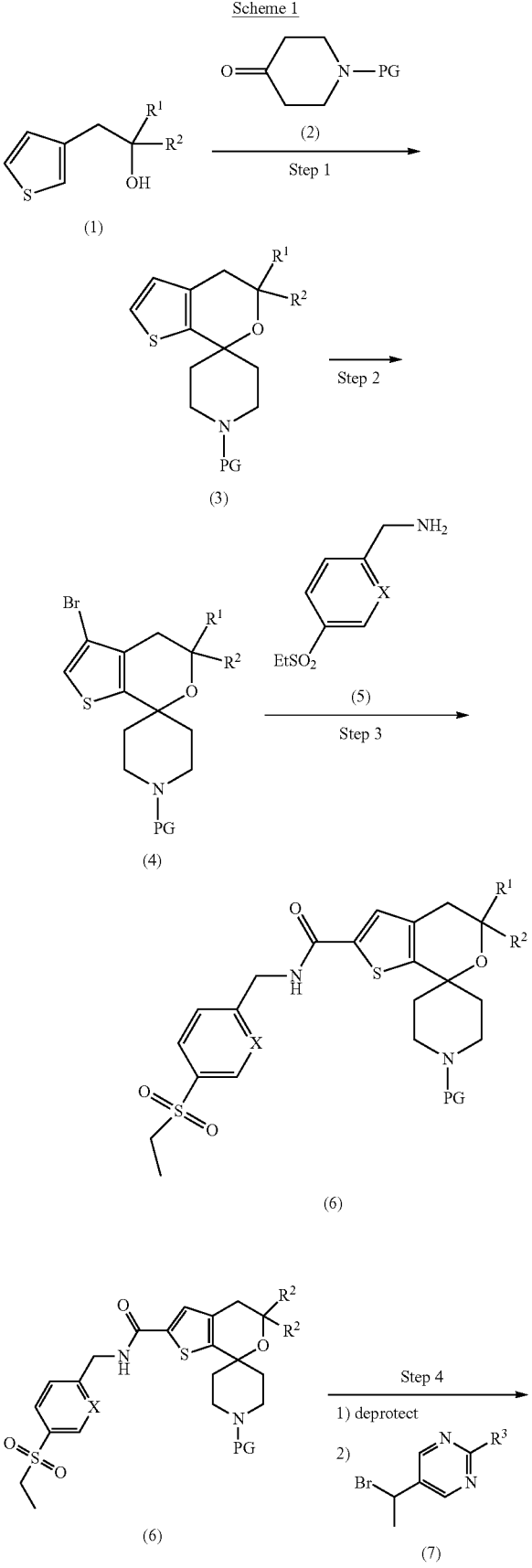

-continued

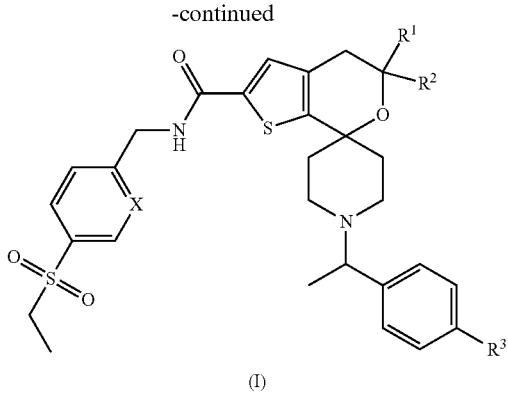

(I)

In scheme 1, PG is an appropriate amine protecting group. Amine protecting groups are well known and appreciated in the art, and may include carbamates and amides. One skilled in the art will recognize alternative reagents and procedures to add and remove said protecting groups. A person skilled in the art will recognize that there are a variety of methods to prepare substituted hydroxyethyl thiophenes. For example, compound (1) may be prepared from a substituted 2-(3-thienyl)acetate with a substituted epoxide in the presence of a strong base such as sec-butyllithium or n-butyllithium at a temperature such as −78 to −60° C., followed by ring opening by a Lewis acid such as boron trifluoride diethyl etherate. In Step 1, the substituted hydroxyethyl thiophene (1) and the protected or unprotected 4-keto piperidine (2) may be combined in the presence of an acid such as trifluoroacetic acid to yield the spirothienylpyrano piperidine (3). In the event that the protecting group, PG, is removed during step 1, the amine in compound (3) may be protected using a standard amine protecting group such as tert-butyloxycarbonyl. In Step 2, compound (3) may be halogenated; for example, compound (3) may be brominated with NBS and a catalyst such as dimethylamino pyridine to give compound (4).

In step 3, compound (4) may be reacted with carbon monoxide and the amine (5) in the presence of an organometallic ligand, such as 4,5-bis-(diphenylphosphino)-9,9-dimethylxanthene and a catalyst, such as palladium(II) acetate, and a base, such as DIPEA, to provide compound (6). The skilled artisan will appreciate that there are alternative ligands and catalysts. Alternatively, in step 3, the bromide of compound (4) may be converted to a carboxylic acid and coupled with the amine (5) under standard coupling conditions. The coupling of a carboxylic acid with an amine (5) can be affected in the presence of a suitable coupling reagent, such as T3P® and a suitable amine base, such as DIPEA. Alternative coupling reagents include HOBt, HBTU, and HOAt and carbodiimides, such as DCC, DIC, EDCI. Alternative bases include trimethylamine and TEA. One skilled in the art will recognize that there are a number of other methods and reagents for amide formation resulting from the reaction of carboxylic acids and amines. Additives such as DMAP may be used to enhance the reactions. Alternatively, compound (5) can be acylated using a substituted acyl chloride of a carboxylic acid compound in the presence of a base, such as TEA or pyridine.

In step 4, compound (6) may be deprotected following appropriate conditions known in the art. For example, a tert-butyloxycarbonyl protecting group may be removed with HCl. The free amine may be alkylated with an appropriately substituted methyl pyrimidine (7), where a halogen such as Br or a sulfonate is a leaving group, in the presence of an organic base such as DIPEA or an inorganic base such as potassium carbonate to provide a compound of Formula (I).

A pharmaceutically acceptable salt of the compounds of the invention, such as a hydrochloride salt, can be formed, for example, by reaction of an appropriate free base of a compound of the invention, an appropriate pharmaceutically acceptable acid such as hydrochloric acid in a suitable solvent such as diethyl ether under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The compounds of the present invention, or salts thereof, may be prepared by a variety of procedures known in the art, some of which are illustrated in the Preparations and Examples below. The specific synthetic steps for each of the routes described may be combined in different ways to prepare compounds of the invention, or salts thereof. The products of each step below can be recovered by conventional methods well known in the art, including extraction, evaporation, precipitation, chromatography, filtration, trituration, and crystallization. The reagents and starting materials are readily available to one of ordinary skill in the art.

The following preparations and examples further illustrate the invention and represent typical synthesis of the compounds of the present invention

PREPARATIONS AND EXAMPLES

Preparation 1

1-(Thiophen-3-ylmethyl)cyclopropanol

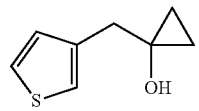

Add titanium(IV) isopropoxide (25 mL, 84.4 mmol) followed by ethylmagnesium bromide in Et$_2$O (3.0 mol/L, 55 mL, 170 mmol) dropwise to a solution of ethyl 2-(3-thienyl) acetate (10 g, 58.74 mmol) in THF (100 mL) cooled with an ice bath to 0° C. Stir the reaction mixture for 5 hours at 0° C., then quench the reaction mixture with ice. Filter the reaction mixture through diatomaceous earth and wash with DCM. Extract the aqueous with DCM (2×), combine the organic extracts, dry over magnesium sulfate, filter, and concentrate to dryness. Purify by silica gel flash chromatography eluting with a gradient of EtOAc/iso-hexane (0:100 to 30:70) to give the title product (7.34 g, 77%). Mass spectrum (m/z): 155 (M+H).

Preparation 2

2-Methyl-1-(thiophen-3-yl)propan-2-ol

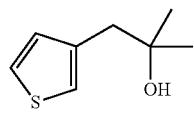

Add lanthanum trichloride lithium chloride complex in THF (0.6 mol/L, 60 mL, 38.412 mmol) to a solution of methyl 2-(3-thienyl)acetate (6 g, 38.41 mmol) in THF (60 mL). Stir the mixture for 40 minutes then add methylmagnesium bromide in Et$_2$O (3.0 mol/L, 38 mL, 115.24 mmol) dropwise and heat to reflux for 1 hour. Cool to 0° C. and quench with the addition of a 1/1 mixture of ice-cold water and brine (100 mL). Extract the mixture with DCM (3×100 mL), combine the organic extracts, filter through a phase separator cartridge, and concentrate to dryness to give the title compound (5.07 g, 84%) as yellow liquid. Mass spectrum (m/z): 139 (M–OH).

Preparation 3

5,5-Dimethyl spiro[4H-thieno[2,3-c]pyran-7,4'-piperidine]

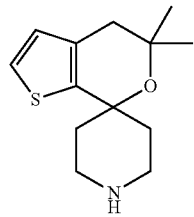 [SMILES: CC1(C)Cc2ccsc2C2(CCNCC2)O1]

Add boron trifluoride diethyl etherate (1.51 mL, 5.60 mmol) at 0° C. to a solution of tert-butyl 4-oxopiperidine-1-carboxylate (2.23 g, 11.2 mmol) and 2-methyl-1-(thiophen-3-yl)propan-2-ol (1.75 g, 11.2 mmol) in toluene (20 mL). Stir for 1 hour at 0° C. then 18 hours at ambient temperature. Heat the reaction at 50° C. 1 hour, then cool to ambient temperature and concentrate to dryness. Dissolve the residue in a minimal amount of MeOH. Load the crude material onto an SCX column, wash with MeOH, elute the product with 2 N ammonia/MeOH, then concentrate to dryness. Purify the crude material with reverse phase chromatography to give the title compound (0.54 g, 16%). Mass spectrum (m/z): 238 (M+H).

Preparation 4

5,5-Cyclopropylspiro[4H-thieno[2,3-c]pyran-7,4'-piperidine

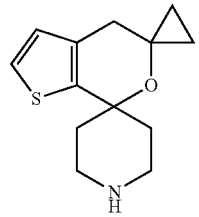 [SMILES: c1cc2c(s1)C1(CCNCC1)OC1(CC1)C2]

Add boron trifluoride diethyl etherate (4.6 mL, 17 mmol) at 0° C. to a solution of tert-butyl 4-oxopiperidine-1-carboxylate (2.23 g, 11.2 mmol) and 1-(thiophen-3-ylmethyl)cyclopropanol (5.2 g, 34 mmol) in toluene (52 mL). Stir for 1 hour at 0° C., 1 hour at ambient temperature, and 1 hour at 50° C. At 50° C., add HCl (4 M in dioxane, 2.1 mL, 8.4 mmol), stir at 50° C. for 1 hour, then cool to ambient temperature and concentrate to dryness. Dissolve the residue in a minimal amount of MeOH. Load the crude material onto an SCX column, wash with MeOH, elute the product with 2 N ammonia/MeOH, then concentrate to dryness to give the title compound (6.10 g, 70%). Mass spectrum (m/z): 236 (M+H).

Preparation 5 tert-Butyl [5,1'-cyclopropane][spiro[4,5-dihydrothieno[2,3-c]pyran-7,4'-piperidine]-1-carboxylate

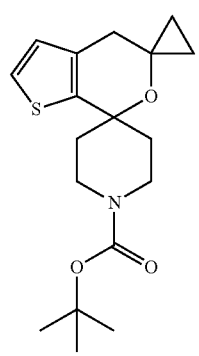 [SMILES: CC(C)(C)OC(=O)N1CCC2(CC1)OC1(CC1)Cc1ccsc12]

Dissolve 5,1'-cyclopropane][spiro[4,5-dihydrothieno[2,3-c]pyran-7,4'-piperidine (5.81 g, 22.23 mmol) in DCM (45 mL), cool to 0° C., then add trimethylamine (15.5 mL, 111.2 mmol) followed by di-tert-butyl dicarbonate (7.35 g, 33.35 mmol). Warm the reaction to ambient temperature and stir 18 hours. Quench with water, separate the layers, and wash with DCM. Combine the organic layers, wash with brine, pass through a phase separator, and concentrate to dryness. Purify with silica gel chromatography with 0-15% EtOAc in hexanes to give the title compound (4.00 g, 51%) as a pale yellow oil. Mass spectrum (m/z): 358 (M+Na).

Preparation 6 tert-Butyl 5,5-dimethylspiro[4H-thieno[2,3-c]pyran-7,4'-piperidine]-1'-carboxylate

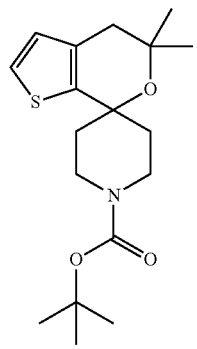 [SMILES: CC(C)(C)OC(=O)N1CCC2(CC1)OC(C)(C)Cc1ccsc12]

Dissolve 5,5-dimethylspiro[4H-thieno[2,3-c]pyran-7,4'-piperidine] (0.54 g, 1.79 mmol) in DCM (10 mL), cool to 0° C., then add trimethylamine (0.50 mL, 3.58 mmol) followed by di-tert-butyl dicarbonate (0.48 g, 2.15 mmol). Warm the reaction to ambient temperature and stir for 18 hours. Quench with water, separate the layers, and wash with DCM. Combine the organic layers, wash with 1 N HCl followed by brine. Pass the material through a phase separator, and concentrate to dryness to give the title compound (0.34 g, 53%) as a pale yellow oil. Mass spectrum (m/z): 238 (M−BOC+H)

Preparation 7 tert-Butyl 2-bromo-5,5-cyclopropyl-spiro[4H-thieno[2,3-c]pyran-7,4'-piperidine]-1'-carboxylate

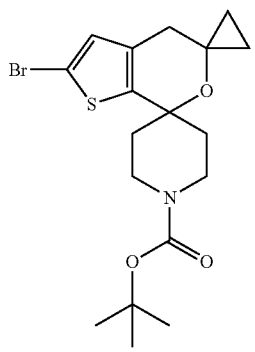

Cool a solution of tert-butyl [5,1'-cyclopropane][spiro[4,5-dihydrothieno[2,3-c]pyran-7,4'-piperidine]-1-carboxylate (1.2 g, 3.4 mmol) in ACN (24 mL) to 0° C. add DMAP (0.042 g, 0.34 mmol) and NBS (1.0 g, 5.8 mmol), and stir for 1 hour. Warm to ambient temperature, stir 30 minutes, then add a mixture of MTBE/iso-hexane (1:2, 45 mL) to the reaction mixture and stir for 30 minutes. Filter off solid. Concentrate filtrate to dryness to obtain the title compound (1.55 g, 77%) as a yellow oil. Mass spectrum (m/z): ($^{79}$Br/$^{81}$Br) 436/438 (M+Na).

Preparation 8 tert-Butyl 2-bromo-5,5-dimethyl-spiro[4H-thieno[2,3-c]pyran-7,4'-piperidine]-1'-carboxylate

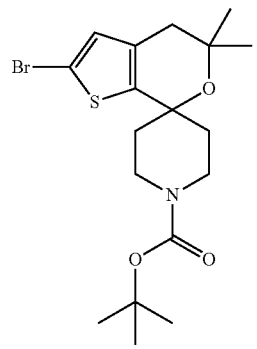 [SMILES: CC(C)(C)OC(=O)N1CCC2(CC1)OC1(CC1)Cc1cc(Br)sc12]

Cool a solution of tert-butyl 5,5-dimethylspiro[4H-thieno[2,3-c]pyran-7,4'-piperidine]-1'-carboxylate (0.34 g, 0.95 mmol) in ACN (3.4 mL) to 0° C., add DMAP (0.012 g, 0.095 mmol) and NBS (0.19 g, 1.05 mmol), and stir for 1 hour. Warm to ambient temperature and concentrate to dryness. Dissolve the residue in DCM, wash with saturate aqueous Na$_2$SO$_3$, filter organic layer through phase separator, and concentrate filtrate to dryness to obtain the title compound (0.41 g, 78%) as a brown oil. Mass spectrum (m/z): ($^{79}$Br/$^{81}$Br) 316/318 (M−BOC).

Preparation 9

5-(Ethylsulfanyl)pyridine-2-carbonitrile

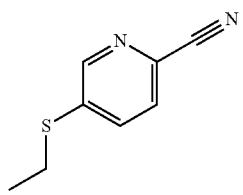

Dissolve 5-bromopyridine-2-carbonitrile (49.42 g, 270.1 mmol) and potassium carbonate (113.5 g, 821.2 mmol) in 1-methyl-2-pyrrolidinone (280 mL) and add ethanethiol (26.4 mL, 356 mmol) in portions over 30 minutes such that the temperature stays below 50° C. Cool the reaction to room temperature and stir overnight. Dilute with EtOAc (1200 mL) and water (2200 mL). Collect the organic layer and wash with brine (3×300 mL), dry the organic layer over sodium sulfate, filter, and concentrate under reduced pressure to give the title compound (44.87 g, 100%) as an off white solid. $^1$H NMR (400.13 MHz, d$_6$-DMSO) δ 8.63 (s, 1H), 7.93 (s, 2H), 3.17 (q, J=7.3, 2H), 1.29 (t, J=7.3, 3H).

Preparation 10

5-(Ethylsulfonyl)pyridine-2-carbonitrile

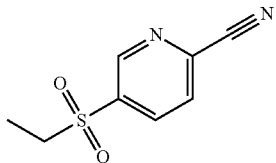

Dissolve 5-(ethylsulfanyl)pyridine-2-carbonitrile (44.36 g, 270.1 mmol) in anhydrous DCM (540 mL) and cool to −20° C. Add 3-chloroperoxybenzoic acid (130 g, 565.0 mmol) in 10-12 gram portions over 1 hour maintaining an internal temperature between 0° C. and −10° C. Stir the reaction mixture in a cold bath allowing to warm to room temperature overnight. Wash with 1 N NaOH (1 L), water, 1 N NaOH (2×500 mL), and brine. Dry the organic layer over sodium sulfate, filter, and concentrate under reduced pressure to give the title compound (49.52 g, 93%) as a white solid. $^1$H NMR (400.13 MHz, $d_6$-DMSO) δ 9.20 (d, J=1.9, 1H), 8.56 (dd, J=2.0, 8.1, 1H), 8.36 (d, J=8.1, 1H), 3.52 (q, J=7.3, 2H), 1.16 (t, J=7.5, 3H).

Preparation 11

1-[5-(Ethylsulfonyl)pyridin-2-yl]methanamine hydrochloride

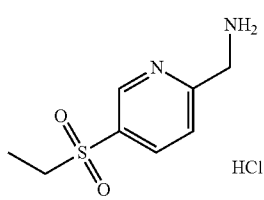

Divide 5-(ethylsulfonyl)pyridine-2-carbonitrile (49.52 g, 252.4 mmol) into three 16.5 g portions. Under $N_2$ in a 2250 mL Parr bottle, add 10% Pd/C (1.65 g, 15.5 mmol) to the vessel and wet with MeOH (750 mL). Add 5-(ethylsulfonyl)pyridine-2-carbonitrile (16.5 g, 84.09 mmol) dissolved in MeOH (750 mL). Add HCl (6 N aqueous, 17.1 ml, 102.6 mmol). Seal the bottle, purge with $N_2$, purge with $H_2$, and pressurize under hydrogen to 68.9 kPa at room temperature for 3 hours. Purge with $N_2$, and then filter the mixture. Repeat on the remaining portions of 5-(ethylsulfonyl)pyridine-2-carbonitrile. Combine all filtrates and concentrate under reduced pressure to give the title compound (59.61 g, 99%) as a beige solid. Mass spectrum (m/z): 201 (M+H—HCl).

Preparation 12

1-[2-(Trifluoromethyl)pyrimidin-5-yl]ethanol

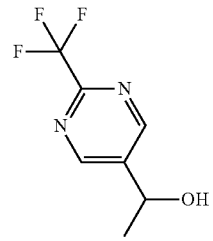

Dissolve 2-(trifluoromethyl)pyrimidine-5-carbaldehyde (11.31 mmol, 1.992 g) in THF (56.56 mL), cool to 0° C., and slowly add methylmagnesium bromide (3 M in $Et_2O$) (33.94 mmol, 11.31 mL). Allow the reaction to warm to room temperature and stir for 2.5 hours. Quench the reaction with 1 N HCl. Add EtOAc and wash with 1 N HCl. Dry the organics over sodium sulfate, filter, and concentrate under reduced pressure to give the title compound (1.66 g, 76.5%). Mass spectrum (m/z): 193.0 (M+H).

Preparation 13

5-(1-Bromoethyl)-2-(trifluoromethyl)pyrimidine

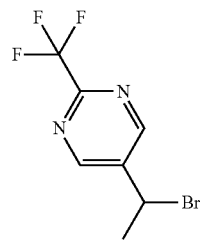

Dissolve 1-[2-(trifluoromethyl)pyrimidin-5-yl]ethanol (1.663 g, 8.655 mmol) and triphenylphosphine (3.405 g, 12.98 mmol) in DCM (86.55 mL) and add NBS (12.98 mmol, 2.311 g) at room temperature. After 3 hours, concentrate the reaction under reduced pressure. Purify the resulting residue via silica gel chromatography eluting with 10% EtOAc/hexanes to give the title compound (1.641 g, 74.34%). $^1$H NMR (400.13 MHz, $d_6$-DMSO) δ 9.26 (s, 2H), 5.63 (q, J=7.0 Hz, 1H), 2.09 (d, J=7.0 Hz, 3H).

Preparation 14 tert-Butyl 2'-({[5-(ethylsulfonyl)pyridin-2-yl]methyl}carbamoyl)-5',5'-dimethyl-4',5'-dihydro-1H-spiro[piperidine-4,7'-thieno[2,3-c]pyran]-1-carboxylate

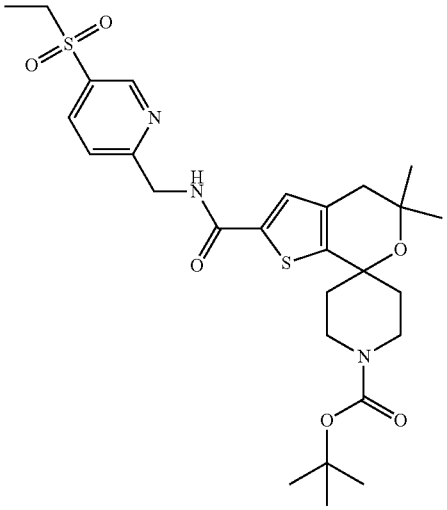 [SMILES: CCS(=O)(=O)c1ccc(CNC(=O)c2cc3c(s2)C2(CCN(C(=O)OC(C)(C)C)CC2)OC(C)(C)C3)nc1]

Add tert-butyl 2-bromo-5,5-dimethyl-spiro[4H-thieno[2,3-c]pyran-7,4'-piperidine]-1'-carboxylate (0.41 g, 0.74 mmol), (5-ethylsulfonyl-2-pyridyl)methanamine; hydrochloride (0.26 g, 1.11 mmol) and DIPEA (0.39 mL, 2.21 mmol) in toluene (4.9 mL) followed by palladium(II) acetate (8.3 mg, 0.036 mmol) and 4,5-bis-(diphenylphosphino)-9,9-dimethylxanthene (0.043 g, 0.074 mmol). Degas the reaction and refill with CO (60 psi) then heat to 90° C. overnight. Cool to ambient temperature. Filter through a pad of diatomaceous earth, wash with DCM (2×20 mL) and concentrate the solvents to give a brown foam. Purify by silica gel flash chromatography eluting with DCM/MeOH (100:0 to 95:5) to give the title product (0.29 g, 52%). Mass spectrum (m/z): 586 (M+Na).

Preparation 15 tert-Butyl 2'-({[5-(ethyl sulfonyl)pyridin-2-yl]methyl}carbamoyl)-1"H,4'H-dispiro[cyclopropane-1,5'-thieno[2,3-c]pyran-7',4"-piperidine]-1"-carboxylate

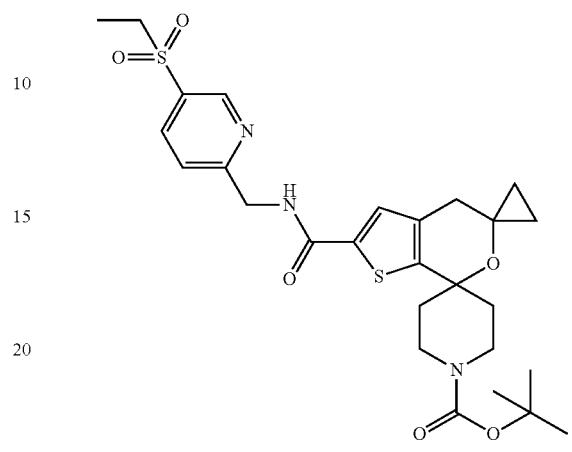

Add tert-butyl 2-bromo-5,5-cyclopropyl-spiro[4H-thieno[2,3-c]pyran-7,4'-piperidine]-1'-carboxylate (2.38 g, 4.19 mmol), (5-ethylsulfonyl-2-pyridyl)methanamine; hydrochloride (1.49 g, 6.29 mmol) and DIPEA (2.21 mL, 12.6 mmol) in toluene (29 mL) followed by palladium(II) acetate (48 mg, 0.21 mmol) and 4,5-bis-(diphenylphosphino)-9,9-dimethylxanthene (0.25 g, 0.42 mmol). Degas the reaction and refill with CO (60 psi) then heat to 90° C. overnight. Cool to ambient temperature. Filter through a pad of celite, wash with DCM (2×20 mL) and concentrate the solvents to give a brown foam. Purify by silica gel flash chromatography eluting with DCM/MeOH (100:0 to 95:5) to give the title product (1.29 g, 49%) as a tan solid. Mass spectrum (m/z): 584 (M+Na).

Prepare the Following Compound Essentially by the Method of Preparation 15

TABLE 1

| Prep No. | Chemical Name | Structure | ES/MS (m/z) (M + 1) |
|---|---|---|---|
| 16 | tert-Butyl 2-[(4-ethylsulfonylphenyl)methylcarbamoyl]-5,5-cyclopropyl-spiro[4H-thieno[2,3-c]pyran-7,4'-piperidine]-1'-carboxylate | 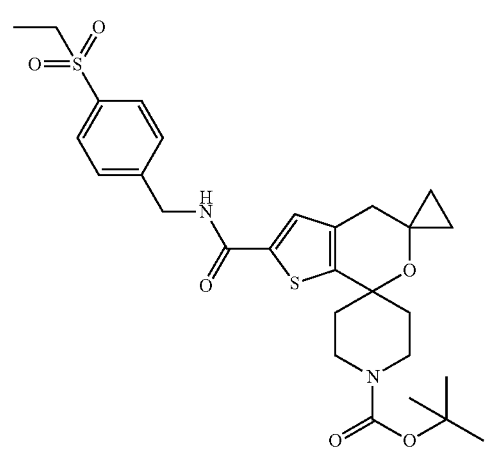 [SMILES: CCS(=O)(=O)c1ccc(CNC(=O)c2cc3c(s2)C2(CCN(C(=O)OC(C)(C)C)CC2)OC2(CC2)C3)nc1] | 561 (M + H) |

Preparation 17

N-{[5-(Ethylsulfonyl)pyridin-2-yl]methyl}-5',5'-dimethyl-4',5'-dihydrospiro[piperidine-4,7'-thieno[2,3-c]pyran]-2'-carboxamide

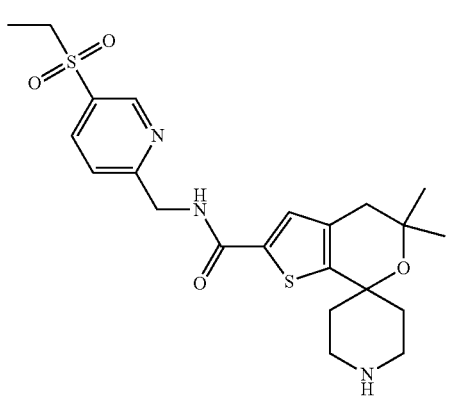 [SMILES: CCS(=O)(=O)c1ccc(CNC(=O)c2cc3c(s2)C2(CCNCC2)OC(C)(C)C3)nc1]

Add HCl in 1,4-dioxane (4 mol/L, 0.74 mL, 2.95 mmol) to a solution tert-butyl 2'-({[5-(ethylsulfonyl)pyridin-2-yl]methyl}carbamoyl)-5',5'-dimethyl-4',5'-dihydro-1H-spiro[piperidine-4,7'-thieno[2,3-c]pyran]-1-carboxylate (0.291 g, 0.38 mmol) in MeOH (10 mL) and heat for 1 hour at 50° C. Concentrate to dryness, load onto a SCX ion exchange column, wash with MeOH, and elute with 2 N ammonia/MeOH to give the title product (0.188 g, 38%). Mass spectrum (m/z): 464 (M+H).

Preparation 18

N-{[5-(Ethylsulfonyl)pyridin-2-yl]methyl}-4'H-dispiro[cyclopropane-1,5'-thieno[2,3-c]pyran-7',4''-piperidine]-2'-carboxamide hydrochloride

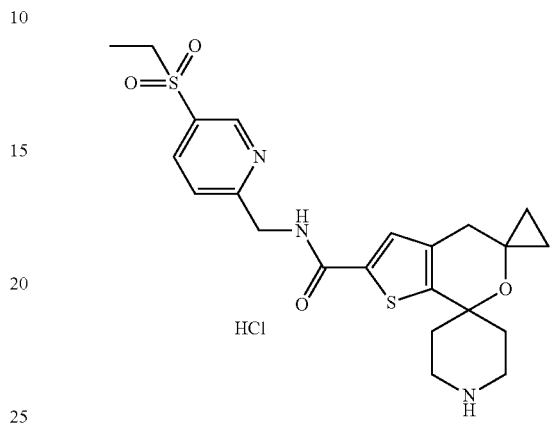

Add HCl in 1,4-dioxane (4 mol/L, 0.86 mL, 3.43 mmol) to a solution tert-butyl 2'-({[5-(ethylsulfonyl)pyridin-2-yl]methyl}carbamoyl)-1''H,4'H-dispiro[cyclopropane-1,5'-thieno[2,3-c]pyran-7',4''-piperidine]-1''-carboxylate (0.43 g, 0.68 mmol) in MeOH (5 mL) and heat for 30 minutes at 50° C. Concentrate to dryness to give the title product (0.34 g, 100%). Mass spectrum (m/z): 462 (M+H—HCl)

Prepare the Following Compound Essentially by the Method of Preparation 18

TABLE 2

| Prep. No. | Chemical Name | Structure | ES/MS (m/z) (M + 1) |
|---|---|---|---|
| 19 | N-[4-(Ethylsulfonyl)benzyl]-4'H-dispiro[cyclopropane-1,5'-thieno[2,3-c]pyran-7',4''-piperidine]-2'-carboxamide hydrochloride | 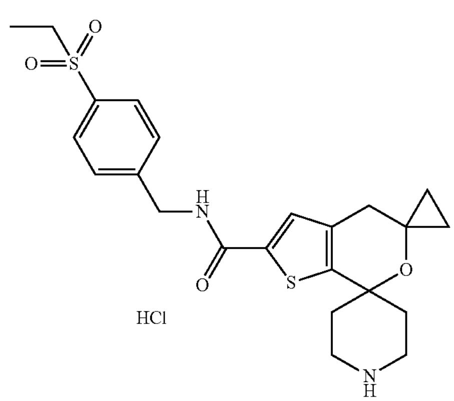 [SMILES: CCS(=O)(=O)c1ccc(CNC(=O)c2cc3c(s2)C2(CCNCC2)OC2(CC2)C3)cc1 ; Cl] | 461 (M + H − HCl) |

Example 1

N-{[5-(Ethylsulfonyl)pyridin-2-yl]methyl}-5',5'-dimethyl-1-{1-[2-(trifluoromethyl)pyrimidin-5-yl]ethyl}-4',5'-dihydrospiro[piperidine-4,7'-thieno[2,3-c]pyran]-2'-carboxamide

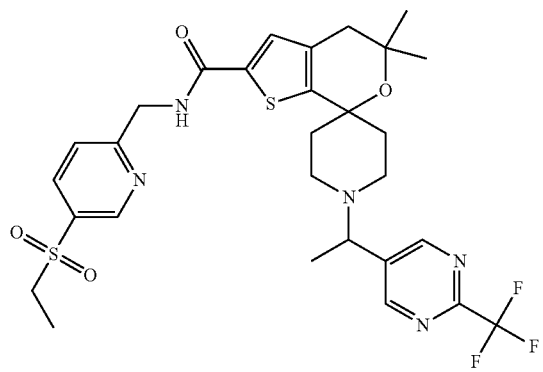 [SMILES: CCS(=O)(=O)c1ccc(CNC(=O)c2cc3c(s2)C2(CCN(C(C)c4cnc(C(F)(F)F)nc4)CC2)OC(C)(C)C3)nc1]

In a microwave vessel, dissolve N-{[5-(ethylsulfonyl)pyridin-2-yl]methyl}-5',5'-dimethyl-4',5'-dihydrospiro[piperidine-4,7'-thieno[2,3-c]pyran]-2'-carboxamide (0.19 g, 0.28 mmol) in acetonitrile (10 mL) and add N,N-diisopropylethylamine (0.64 mL, 3.69 mmol) followed by 5-(1-bromoethyl)-2-(trifluoromethyl)pyrimidine (0.24 g, 0.96 mmol). Seal the vessel and heat at 60° C. for 1 hour, then cool to ambient temperature and concentrate to dryness. Dissolve the residue in DCM, wash with water, filter through a phase separator, and concentrate the organic layer to dryness. Purify the residue by silica gel flash chromatography eluting with DCM/MeOH (100:0 to 95:5). Purify with reverse phase chromatography to give the title product (0.14 g, 49%). Mass spectrum (m/z): 638 (M+H).

Example 2

N-{[5-(Ethylsulfonyl)pyridin-2-yl]methyl}-1"-{1-[2-(trifluoromethyl)pyrimidin-5-yl]ethyl}-4'H-dispiro[cyclopropane-1,5'-thieno[2,3-c]pyran-7',4"-piperidine]-2'-carboxamide

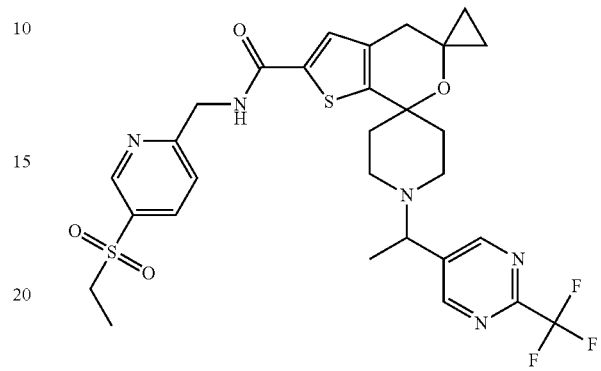

In a microwave vessel dissolve N-{[5-(ethylsulfonyl)pyridin-2-yl]methyl}-4'H-dispiro[cyclopropane-1,5'-thieno[2,3-c]pyran-7',4"-piperidine]-2'-carboxamide hydrochloride (0.34 g, 0.69 mmol) in acetonitrile (5 mL) and add N,N-diisopropylethylamine (0.72 mL, 4.12 mmol) followed by 5-(1-bromoethyl)-2-(trifluoromethyl)pyrimidine (0.22 g, 0.86 mmol). Seal the vessel and heat at 60° C. for 1 hour, then cool to ambient temperature and concentrate to dryness. Dissolve the residue in MeOH, load onto a SCX column, wash with MeoH, then elute with 2 N ammonia in MeOH. Concentrate the ammonia layer to dryness and purify by silica gel flash chromatography eluting with DCM/MeOH (100:0 to 95:5) to give the title product (0.37 g, 86%). Mass spectrum (m/z): 636 (M+H).

Prepare the Following Compound Essentially by the Method of Example 2

TABLE 3

| Ex No. | Chemical Name | Structure | ES/MS (m/z) (M + H) |
|---|---|---|---|
| 3 | 1"-[1-(4-Cyanophenyl)ethyl]-N-[4-(ethylsulfonyl)benzyl]-4'H-dispiro[cyclopropane-1,5'-thieno[2,3-c]pyran-7',4"-piperidine]-2'-carboxamide | 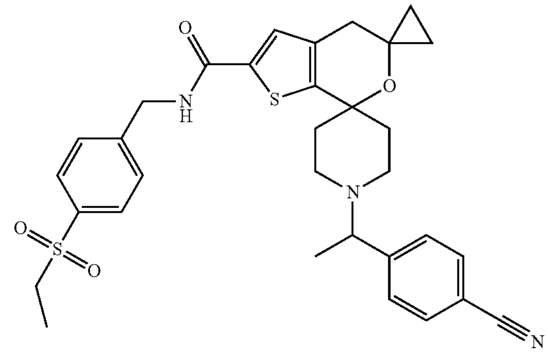 [SMILES: CCS(=O)(=O)c1ccc(CNC(=O)c2cc3c(s2)C2(CCN(C(C)c4ccc(C#N)cc4)CC2)OC2(CC2)C3)cc1] | 590.2 (M + H) |

Example 4

N-{[5-(Ethyl sulfonyl)pyridin-2-yl]methyl}-5',5'-dimethyl-1-{(1S)-1-[2-(trifluoromethyl)pyrimidin-5-yl]ethyl}-4',5'-dihydrospiro[piperidine-4,7'-thieno[2,3-c]pyran]-2'-carboxamide

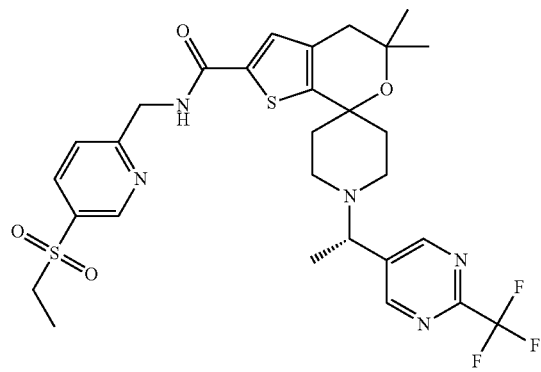 [SMILES: CCS(=O)(=O)c1ccc(CNC(=O)c2cc3c(s2)C2(CCN([C@@H](C)c4cnc(C(F)(F)F)nc4)CC2)OC(C)(C)C3)nc1]

Example 5

N-{[5-(Ethylsulfonyl)pyridin-2-yl]methyl}-5',5'-dimethyl-1-{(1R)-1-[2-(trifluoromethyl)pyrimidin-5-yl]ethyl}-4',5'-dihydrospiro[piperidine-4,7'-thieno[2,3-c]pyran]-2'-carboxamide

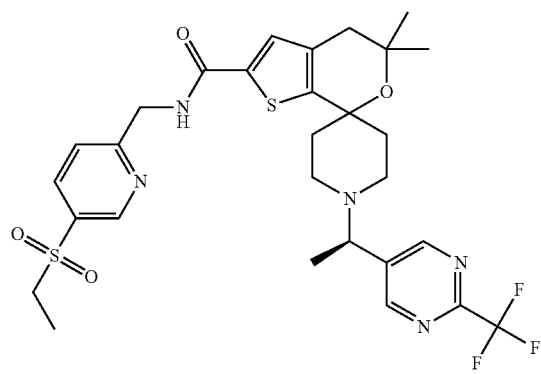 [SMILES: CCS(=O)(=O)c1ccc(CNC(=O)c2cc3c(s2)C2(CCN([C@H](C)c4cnc(C(F)(F)F)nc4)CC2)OC(C)(C)C3)nc1]

Solubilize N-{[5-(ethylsulfonyl)pyridin-2-yl]methyl}-5',5'-dimethyl-1-{1-[2-(trifluoromethyl)pyrimidin-5-yl]ethyl}-4',5'-dihydrospiro[piperidine-4,7'-thieno[2,3-c]pyran]-2'-carboxamide (138 mg, 0.217 mmol) in MeOH (10.5 mL). Separate the isomers with chiral chromatography by HPLC [Chiralpak IA column (30×250 mm) with 50% ACN:50% IPA (with 0.2% IPAm) at 68 mL/min, UV detection at 225 nm (monitored at 250 nm)]. Analytical conditions: 45% IPA (0.2% IPAm) in ACN 5.0 mL/min, Chiralpak column [IA (4.6×150 mm)] detection at 204 nm. Combine pure fractions, concentrate to dryness, and lyopholyze to obtain pale yellow solids, Example 4, (47 mg, 34% yield, de>99%, $R_t$=2.01 minutes), mass spectrum (m/z): 638 (M+H). Example 5, (45 mg, 32% yield, de>99%, $R_t$=2.97 minutes), mass spectrum (m/z): 638 (M+H). Assign the absolute configuration of these materials via VCD. VCD-spectrometer=ChirallR-X with DualPEM; 4.0 mg/100 μL, resolution=4 cm$^{-1}$; PEM=1400 cm$^{-1}$; 72000 scans, 24 hours; BaF$_2$ cell, path length=100 μm. Force fields used in MolMec calculations=MMF94S, MMFF, SYBYL. Methodology and basis set for DFT calculations=SCRF-B3LYP/6-31G(d), SCRF-B3PW91/6-31G(d). Confidence level=99%.

Example 6

N-{[5-(Ethylsulfonyl)pyridin-2-yl]methyl}-1"-{(1S)-1-[2-(trifluoromethyl)pyrimidin-5-yl]ethyl}-4'H-dispiro[cyclopropane-1,5'-thieno[2,3-c]pyran-7',4"-piperidine]-2'-carboxamide

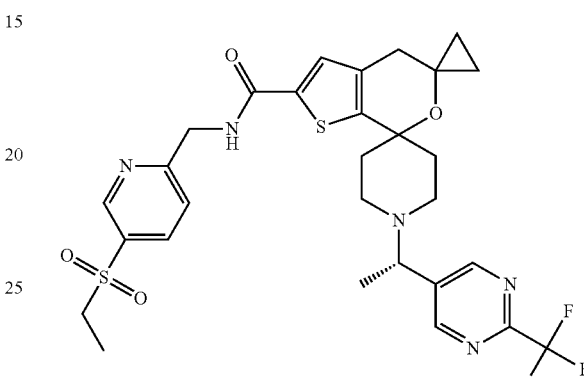

Example 7

N-{[5-(Ethylsulfonyl)pyridin-2-yl]methyl}-1"-(1R)-1-[2-(trifluoromethyl)pyrimidin-5-yl]ethyl-4'H-dispiro[cyclopropane-1,5'-thieno[2,3-c]pyran-7',4"-piperidine]-2'-carboxamide

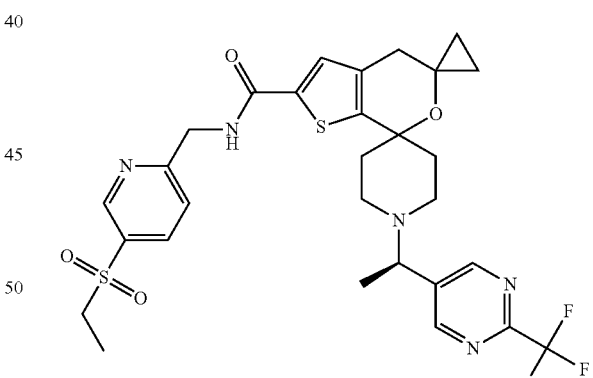

Solubilize N-{[5-(ethylsulfonyl)pyridin-2-yl]methyl}-1"-{1-[2-(trifluoromethyl)pyrimidin-5-yl]ethyl}-4'H-dispiro[cyclopropane-1,5'-thieno[2,3-c]pyran-7',4"-piperidine]-2'-carboxamide (369 mg, 0.581 mmol) in MeOH (22 mL) and filter the solution. Separate the isomers with chiral chromatography by HPLC [Chiralpak IC column (30×250 mm) with 50% ACN:50% IPA (with 0.2% IPAm) at 130 mL/min, inject 2.0 mL every 9.7 min, UV detection at 225 nm]. Analytical conditions: 45% IPA (0.2% IPAm) in ACN 5.0 mL/min, Chiralpak column [IA (4.6×150 mm)] detection at 204 nm. Combine pure fractions, concentrate to dryness, and lyopholyze to obtain pale yellow solids. Example 6, (146 mg, 39% yield, de>99%, $R_t$=1.61 minutes), mass spectrum (m/z): 636 (M+H). Example 7, (143 mg, 37% yield, de>98%, $R_t$=2.02 minutes), mass spectrum (m/z): 636 (M+H). Assign the absolute configuration of these materials via VCD. VCD-spectrometer =ChirallR-X with DualPEM; 4.0 mg/100 µL, resolution=4 cm$^{-1}$; PEM=1400 cm$^{-1}$; 72000 scans, 24 hours; BaF$_2$ cell, path length=100 µm. Force fields used in MolMec calculations=MMF94S, MMFF, SYBYL. Methodology and basis set for DFT calculations=SCRF-B3LYP/6-31G(d), SCRF-B3PW91/6-31G(d). Confidence level=99%.

Purify the following compounds essentially by the method of Examples 6 and 7 using HPLC chiral.

rophenyl)-5-isopropyl-isoxazol-4-yl]methoxy]-N,2-dimethyl-anilino]methyl]benzoic acid for beta binding, and 6 nM [$^3$H]-25-hydroxycholesterol for gamma binding, and 0.5 µg RORa receptor, 0.03 µg RORb receptor, or 0.13 µg RORg receptor per well. Assays are typically run in 96-well format. Competing test compounds are added at various concentrations ranging from about 0.4 nM to 25 µM. Non-specific binding is determined in the presence of 250 nM 25-hydroxycholesterol for RORa and RORg binding, 250 nM 3-[[4-[[3-(2,6-dichlorophenyl)-5-isopropyl-isoxazol-4-yl]methoxy]-N,2-dimethyl-anilino]methyl]benzoic acid for RORb binding. The sample, label and receptor solutions are combined in a 96 well assay plate (Costar 3632) and

TABLE 4

| Ex No. | Chemical Name | Structure | ES/MS (m/z) (M + H) |
|---|---|---|---|
| 8 | 1'-[1-(4-Cyanophenyl)ethyl]-5,5-spirocyclopropane-N-[(4-ethylsulfonylphenyl)methyl]spiro[4H-thieno[2,3-c]pyran-7,4'-piperidine]-2-carboxamide isomer 1 | 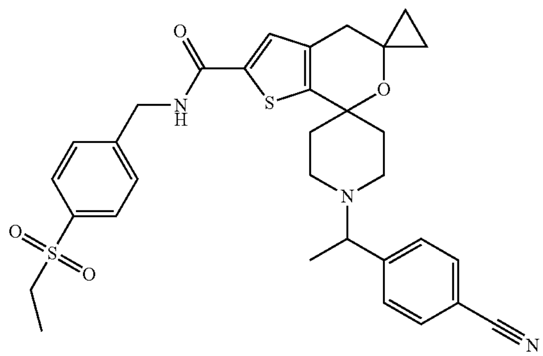 [SMILES: CCS(=O)(=O)c1ccc(CNC(=O)c2cc3c(s2)C2(CCN(C(C)c4ccc(C#N)cc4)CC2)OC2(CC2)C3)cc1] | 590 (M + H) |
| 9 | 1'-[1-(4-Cyanophenyl)ethyl]-5,5-spirocyclopropane-N-[(4-ethylsulfonylphenyl)methyl]spiro[4H-thieno[2,3-c]pyran-7,4'-piperidine]-2-carboxamide isomer 2 | 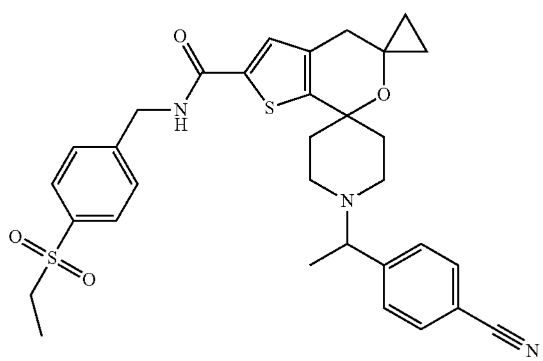 [SMILES: CCS(=O)(=O)c1ccc(CNC(=O)c2cc3c(s2)C2(CCN(C(C)c4ccc(C#N)cc4)CC2)OC2(CC2)C3)cc1] | 590 (M + H) |

Biological Assays

RORa, b, and g Binding Inhibitors

His-tagged human RAR-related orphan receptor alpha (hRORa), human RAR-related orphan receptor beta (hRORb), and human RAR-related orphan receptor gamma (hRORg) are used for receptor-ligand competition binding assays to determine $K_i$ values. Typical procedures are provided below.

Receptor competition binding assays are run in a buffer made up of DPBS (1 L) (Hyclone #SH30028.03), 2.2 g BSA Fraction v (Roche #9048-46-8), 100 mL glycerol (Fischer #56-81-5) and 40 mL DMSO (reagent grade). The final wells contain 20 µg/mL aprotinin and 20 µg/mL leupeptin and 10 µM Pefabloc. Typically, receptor binding assays include radio-labeled ligands, such as 7 nM [$^3$H]-25-hydroxycholesterol for alpha binding, 20 nM [$^3$H]-3-[[4-[[3-(2,6-dichloincubated overnight at room temperature, then 25 µl beads (Amersham YSi (2-5 micron) copper His-tag Spa Beads, #RPNQ0096) for a final bead concentration of 1 mg/well is added to each reaction. Plates are mixed for 30 minutes on an orbital shaker at room temperature. After an incubation of 4 hours, plates are read in a Wallac MICROBETA® counter.

The data are used to calculate an estimated IC$_{50}$ using a four parameter logistic fit. The Kd for [$^3$H]-25-hydroxycholesterol for RORa and RORg, and [$^3$H]-3-[[4-[[3-(2,6-dichlorophenyl)-5-isopropyl-isoxazol-4-yl]methoxy]-N,2-dimethyl-anilino]methyl]benzoic acid for RORb binding, is determined by saturation binding. The IC$_{50}$ values for compounds are converted to Ki using the Cheng-Prushoff equation.

The results of the following exemplified compounds are shown in Table 5 below.

TABLE 5

| Example # | RORa Ki (nM) | RORb Ki (nM) | RORg Ki (nM) |
|---|---|---|---|
| 5 | 5679 ± 2132, n = 2 | >12500 | 6.96 ± 3.89, n = 2 |
| 7 | 3461 | >12500 | 6.401 ± 2.618, n = 2 |
| 8 | >20390 | >12500 | 6.00 ± 1.81, n = 2 |

Mean ± standard deviation

These results demonstrate that the compounds of Table 5 are selective for RORg versus RORa and RORb.

HEK293 RORg GAL4 Receptor-Reporter Assay

As an indicator of inverse agonist activity, an RAR-related orphan receptor gamma (RORg) receptor-reporter assay (RORg-GAL4/pGL4.31) is performed in HEK293 cells. HEK293 cells are co-transfected using Fugene™ reagent. A reporter plasmid containing a GAL4 binding domain and a minimal adenoviral promoter upstream of a firefly luciferase gene is co-transfected with a plasmid constitutively expressing a human RORg ligand binding domain fused to yeast GAL4 DNA binding domain. Cells are transfected in T150 $cm^2$ flasks in MEM media without FBS. After 18 hours incubation, transfected cells are trypsinized, plated in 96-well microtiter plates in 3:1 DMEM-F12 media containing 10% FBS, incubated for 4 hours and then exposed to various concentrations of test compounds ranging from about 0.05 nM to 10 µM. After 18 hours of incubations with compounds, cells are lysed and luciferase activity is quantified using standard techniques. Data is fit to a 4 parameter-fit logistics to determine $IC_{50}$ values.

The results of the following exemplified compounds are shown in Table 6 below.

TABLE 6

| Example # | $hIC_{50}$ (nM) |
|---|---|
| 5 | 16.68 ± 20.28, n = 4 |
| 7 | 22.34 ± 23.79, n = 4 |
| 8 | 34.41 ± 6.01, n = 2 |

Mean ± standard deviation

These results demonstrate that the compounds of Table 6 are inverse agonists for human RORg receptor.

PBMC IL-17 Secretion ELISA and Cell TiterGlo Viability Assay

PBMC's are isolated from whole blood buffy coats by first combining fresh buffy coats with equal volumes of phosphate buffered saline. Thirty five mL of PBS/buffy coat solution are then gently overlaid onto 15 mL of Ficoll in 50 mL conical tubes. Following centrifugation for 30 minutes at 500×g (with slow acceleration and deceleration) the top layer of plasma is discarded and the layer of cells along the Ficoll interface is collected and pooled. Each 250 mL tube is filled to the top with room temperature RPMI-1640 media. Tubes are spun for 10 minutes at 500×G (with slow acceleration and deceleration), the media is removed by aspiration, and the wash step is repeated. Cells are resuspended in ice cold Recovery Cell Culture Freezing Medium from Life Technologies (Catalog number 12648-010) on ice. The cell concentration is adjusted to 66.7 million cells/mL. Cell are slow frozen at −1° C./minute in vials with 100 million cells and stored in liquid nitrogen.

Stimulation of IL-17 Secretion and Compound Addition

PBMC are brought out of thaw by resuspending with 1 mL of complete media (RPMI-1640 containing 30 mM HEPES, 100 units/mL penicillin, 100 µg/mL streptomycin, 3.25 mM L-Glutamine, 0.2 µM beta-mercaptoethanol, and 10% FBS) followed by the drop wise addition of 2 mL, 4 mL, 8 mL, and 16 mL of complete media with gentle swirling. Cells are spun down for 5 minutes and the cell pellet is resuspended in complete media. Clumps of cells are broken up by running the cell solution through a 23 gauge syringe needle and a 40 µM cell strainer. One hundred thousand cells per well are added to 384 well polystyrene tissue culture treated flat bottomed plates in a total of 30 µL. Stimulation cocktail containing anti-human CD3 antibody, anti-human CD28 antibody, IL-23 and compounds prepared in complete media are added to the cells simultaneously in a total volume of 30 µL. The final concentration of added stimulants is 160 ng/mL, 500 ng/mL, and 5 ng/mL for anti-CD3 antibody, anti-CD28 antibody, and IL-23 respectively and 0.3% for DMSO. Plates are sealed with AERASEAL® sealing film and incubated for 48 hours at 37° C., 95% humidity, and 5% $CO_2$.

Following the incubation period the plates are spun at 200×g for five minutes. Supernatants are diluted 1:1 with equal volume 1% BSA/PBS and tested for IL-17 with a human IL-17 ELISA kit from R&D system (catalog #D317E) according to the protocol provided with the kit with one exception—the colorimetric substrate OPD (o-phenylenediamine dihydrochloride, Sigma Cat #P6912) is used instead of the substrate supplied in the kit. Absorbance at 492 nm is measured with the Envision multi-label plate reader. A492 values are converted to concentration of IL-17 based on the IL-17 standard curve as shown below: pg/mL IL-17=EC50*[[(Top-Bottom)/(A492-Bottom)]-1](1/−Hill).

$IC_{50}$'s for inhibition of IL-17 secretion is calculated based on converted values using a standard 4-parameter fit with maximum inhibition determined from the average values of wells with no added stimulants nor compounds and minimum inhibition from the average values of wells with stimulants alone and no added compound.

Equal volumes of Cell TITERGLO® cell viability testing reagent (Promega Cat #G7573) are added to the cells remaining in the plates, and following a fifteen minute incubation with gentle shaking at room temperature luminescence is measured with the Envision multi-label plate reader. Percent cell death is calculated by setting 100% activity (cell death) to zero luminescence units and minimum activity (max number of viable cells) as the average luminescence units of wells containing stimulants alone and no added compound. $IC_{50}$'s are calculated using a standard four parameter fit.

The results of the following exemplified compounds are shown in Table 7 below.

TABLE 7

| Example # | hPBMC IL-17 ELISA ($EC_{50}$, nM) | Cell TiterGlo Viability ($EC_{50}$, µM) |
|---|---|---|
| 5 | 10.97 ± 7.67, n = 5 | >1.0 |
| 7 | 14.61 ± 8.24, n = 8 | >1.0 |
| 8 | 10.94 ± 6.44, n = 6 | >1.0 |

Mean ± standard deviation

We claim:

1. A compound of formula

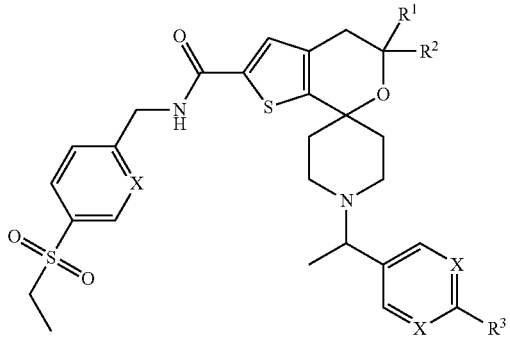

wherein

X is independently —N— or —CH—;

R¹ and R² are both CH₃; or R¹ and R² can be joined together to form a three-membered carbocyclic ring;

R³ is —CN or —CF₃;

or a pharmaceutically acceptable salt thereof.

2. The compound of claim 1 that is N-{[5-(Ethylsulfonyl)pyridin-2-yl]methyl}-5',5'-dimethyl-1-{(1R)-1-[2-(trifluoromethyl)pyrimidin-5-yl]ethyl}-4'5'-dihydrospiro[piperidine-4,7'-thieno[2,3-c]pyran]-2'-carboxamide:

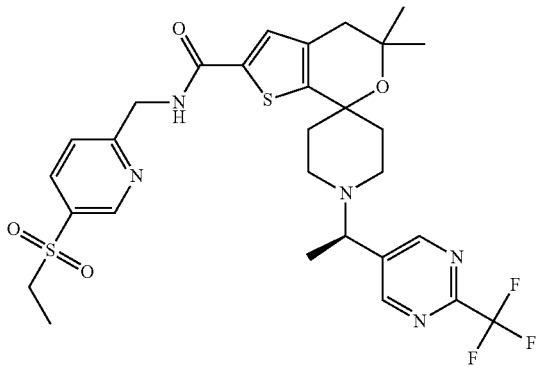 [SMILES: CCS(=O)(=O)c1ccc(CNC(=O)c2cc3c(s2)C2(CCN([C@H](C)c4cnc(C(F)(F)F)nc4)CC2)OC(C)(C)C3)nc1]

or a pharmaceutically acceptable salt thereof.

3. The compound of claim 1 that is N-{[5-(Ethylsulfonyl)pyridin-2-yl]methyl}-1''-{(1R)-1-[2-(trifluoromethyl)pyrimidin-5-yl]ethyl}-4'H-1-dispiro[cyclopropane-1,5'-thieno[2,3-c]pyran-7',4''-piperidine]-2'-carboxamide:

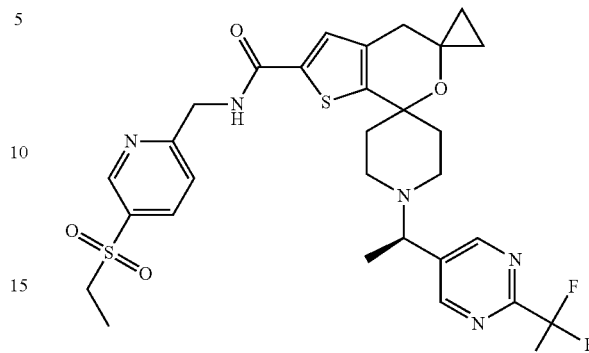

or a pharmaceutically acceptable salt thereof.

4. A pharmaceutical composition comprising a compound of claim 1, or a pharmaceutically acceptable salt thereof, in combination with one or more pharmaceutically acceptable carriers, diluents, or excipients.

5. The pharmaceutical composition according to claim 4 comprising one or more other therapeutic agents.

6. A method of treating psoriasis comprising administering a compound of claim 1, or a pharmaceutically acceptable salt thereof, to a patient in need thereof.

7. A method of treating seronegative spondylarthropathies comprising administering a compound of claim 1, or a pharmaceutically acceptable salt thereof, to a patient in need thereof.

8. The method according to claim 7 for treating axial spondyloarthritis, ankylosing spondylitis, or psoriatic arthritis.

9. The compound according to claim 1 wherein R³ is CF₃.

10. The compound according to claim 9 wherein X is N.

11. The compound according to claim 10 wherein R¹ and R² are both CH₃.

12. The compound according to claim 10 wherein R¹ and R² are joined together to form a three-membered carbocyclic ring.

13. The compound according to claim 1 wherein R³ is CN.

14. The compound according to claim 13 wherein X is —CH—.

15. The compound according to claim 14 wherein R¹ and R² are joined together to form a three-membered carbocyclic ring.

* * * * *